(12) United States Patent
Smith et al.

(10) Patent No.: US 6,583,160 B2
(45) Date of Patent: *Jun. 24, 2003

(54) NICOTINE THERAPY METHOD AND ORAL CARRIER FOR ASSUAGING TOBACCO-ADDICTION

(76) Inventors: Steve Smith, 5100 Channel Ave., Richmond, CA (US) 94804; Paul C. Wilhelmsen, 281 Livorna Heights, Alamo, CA (US) 94507

( * ) Notice: Subject to any disclaimer, the term of this patent is extended or adjusted under 35 U.S.C. 154(b) by 0 days.

This patent is subject to a terminal disclaimer.

(21) Appl. No.: 09/938,375

(22) Filed: Aug. 23, 2001

(65) Prior Publication Data

US 2002/0002189 A1 Jan. 3, 2002

Related U.S. Application Data

(63) Continuation-in-part of application No. 09/771,454, filed on Jan. 29, 2001, now abandoned, which is a continuation-in-part of application No. 09/292,045, filed on Apr. 14, 1999, now Pat. No. 6,248,760.

(51) Int. Cl.$^7$ .................. A61K 31/465; A61K 9/20; A61K 47/00
(52) U.S. Cl. .................. 514/343; 424/434; 424/435; 424/464; 424/465; 424/474; 424/479; 514/772; 514/772.4; 514/777; 514/784; 514/810; 514/813; 514/960; 514/974
(58) Field of Search .................. 514/343, 769, 514/810, 813, 819, 990, 772, 772.4, 777, 784, 974; 424/434, 435, 464, 466, 468, 471, 472, 474, 682, 686, 687, 688, 692, 465, 475, 479

(56) References Cited

U.S. PATENT DOCUMENTS

| 4,953,572 A | * | 9/1990 | Rose et al. ................. 131/270 |
| 5,824,334 A |   | 10/1998 | Stanley et al. ............... 424/440 |
| 6,248,760 B1 |  | 6/2001 | Wilhelmsen ................ 514/343 |

FOREIGN PATENT DOCUMENTS

| EP | 0 526 524 | * 12/1995 |

\* cited by examiner

Primary Examiner—José G. Dees
Assistant Examiner—Frank Choi
(74) Attorney, Agent, or Firm—Richard B. Main

(57) ABSTRACT

A method for assuaging tobacco addiction comprises pulsing doses of nicotine into a user's bloodstream so it reaches the brain before passing through the liver. A nicotine-burst tablet is held in the mouth by a user to receive each nicotine-pulse dose. The tablet is configured to suddenly release its entire nicotine payload from an otherwise inert or benign material. Such nicotine payload is relatively small, e.g., under one milligram. The therapeutic effects depend on the change of nicotine levels in the blood over a change in time. Rapid nicotine onset of a small dose is more assuaging than a slow build-up to a high dosage. An oral carrier comprises a nicotine saturated instant-dissolve paper that delivers one nicotine pulse. An additive prevents abuse by causing excessive use to catalyze a foul taste or sickening sensation.

4 Claims, 1 Drawing Sheet

NICOTINE THERAPY METHOD AND ORAL CARRIER FOR ASSUAGING TOBACCO-ADDICTION

RELATED APPLICATIONS

This Application is a continuation-in-part of U.S. patent application Ser. No. 09/771,454, filed Jan. 29, 2001, now abandoned, and which is, in turn, a continuation-in-part of U.S. patent application Ser. No. 09/292,045, filed Apr. 14, 1999, and now issued as U.S. Pat. No. 6,248,760, on Jun. 19, 2001. Such are incorporated herein by reference.

BACKGROUND OF THE INVENTION

1. Field of the Invention

The present invention relates to tobacco-addiction therapies, and more particularly to methods and devices for assuaging nicotine cravings in users.

2. Description of Related Art

Tobacco-addiction is a serious health problem through out the world. The hundreds of compounds carried along with the nicotine cause most of the trouble, but the nicotine is responsible for the chemical addiction. Tobacco users find it too difficult to quit because both the nicotine cravings and ritual behaviors are too severe and ingrained. The prior art has therefore developed a multitude of therapies, devices, and methods for helping people quit tobacco. Many of them follow similar ritual patterns of putting things in the mouth.

Given the large number of users who continue using tobacco, it can be assumed that no prior art attempt has been completely successful.

Many smokers have decided to continue smoking, no matter what. But recent changes in social behavior and even the Law have put many places out-of-bounds for smokers, e.g., commercial airflights, restaurants, school, work, home, etc. So in these situations, such smokers need a temporary relief from the pains of abstinence. Others wanting to quit altogether also need effective relief from cravings.

One line of therapy for tobacco-addiction is aversion therapy. An attempt is preferably made to associate some ill-effect whenever the user engages in the addiction. For example, ANTABUSE is a brand of tetraethylthiuram disulfide that will induce nausea, vomiting, and headache if the user drinks alcohol. A chemical reaction in the bloodstream generates acetaldehyde, and it's this compound that produces the aversive symptoms. A similar, less severe aversion therapy is known as TEMPOSIL, e.g., citrated calcium carbamide.

Conventional behavioral aversion therapies also include hypnosis and electroshock. In hypnosis, a suggestion is preferably made to quit tobacco outright, or associate it with a bad taste or smell. In electroshock therapy, a harmless shock is sent, for example, to punish the user each time a cigarette is smoked. An interesting observation is made by W. L. Jenkins, combinations of warm heat and shock are interpreted as hot. (*Journal of Experimental Psychology,* 1938, v22:564–572.) So a more effective, but harmless electroshock therapy would include the application of warm heat, perhaps even constant warm heat punctuated by the shocks.

Theodore Stanley, et al., observed in U.S. Pat. No. 5,824,334, issued Oct. 20, 1998, that heavy smokers seem to adjust their levels of nicotine in their blood to stay within narrow limits. They also state that "a smoker's craving for tobacco is not mitigated by a relatively low, constant level of nicotine." When nicotine is received through smoking, the rapid absorption of the nicotine through the lungs results in an initial peak of nicotine which then trails off. The blood-level concentration peak produced by cigarettes is higher and sharper than steadier levels obtained from patches or gums. Such initial peak is said to be 30–40 nanograms per milliliter of blood, and is reached within ten minutes. So Stanley, et al., concluded that quick-rise effects are probably necessary for more complete relief from craving in the early stages of withdrawal.

One of the present inventors, Paul Wilhelmsen, was issued U.S. Pat. No. 6,248,760, on Jun. 19, 2001. It describes a tablet giving rapid release of nicotine for transmucousal administration. He says quick-rise effects are necessary for relief from craving. A nicotine layer in an oral tablet is designed to be rapidly absorbed through the tissues inside the user's mouth.

SUMMARY OF THE INVENTION

Briefly, a method and oral tablet embodiment of the present invention comprise a flash dissolve nicotine payload disposed in a delivery carrier that is then placed in the mouth of a user. For example, a pill, tablet, or capsule is a suitable oral delivery form. The nicotine payload liberates from its fixing with the delivery carrier all at once sometime after being wetted inside the mouth. The result is a short, intense nicotine dose pulse that enters the bloodstream and circulates to the brain before being filtered out by the liver. Such rapid spiking of nicotine mimics that received from a single puff of a cigarette. Multiple bursts are received by multiple takings.

In alternative embodiments of the present invention, a plurality of flash dissolve nicotine payloads are carried in time-release envelopes that burst sequentially over time. The number of bursts and interval time between them are similar to those obtained from the ordinary smoking of one whole cigarette.

An advantage of the present invention is a method and oral tablet are provided for relief of cravings in a tobacco-addicted user.

Another advantage of the present invention is that a method and oral tablet are provided for more satisfying delivery of nicotine to the brain of an addicted user.

A still further advantage of the present invention is that a method and oral tablet are provided for cigarette smokers wishing to quit.

Another advantage of the present invention is that a method and oral tablet are provided for cigarette smokers wishing to bridge over periods when they cannot smoke a cigarette.

An advantage of the present invention is a method and oral tablet are provided for pulsing nicotine into the blood-flow to the brain of a user.

The above and still further objects, features, and advantages of the present invention will become apparent upon consideration of the following detailed description of specific embodiments thereof, especially when taken in conjunction with the accompanying drawings.

DETAILED DESCRIPTION OF THE INVENTION

Figure 1:
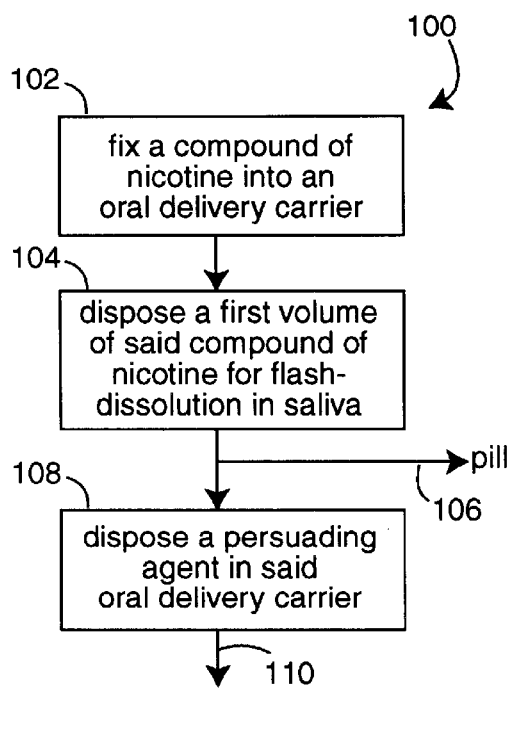
FIG. 1 is a flowchart of a means for abstaining from tobacco-use embodiment of the present invention.

FIG. 1 represents a means for abstaining from tobacco use, and is referred to herein by the general reference numeral 100. Such comprises a means 102 for fixing a compound of nicotine to an oral delivery carrier, e.g. to enable easy counting, measurement, and placement in a user's mouth. A means 104 for disposing a part of such fixed nicotine is included, and it is important that such provides for a flash-dissolution in saliva of all such part. Since a tablet or pill is a usual form of carrier, a single coating or layer with high surface area relative to erosion depth is needed. The whole surface area is preferably exposed to the user's saliva all-at-once, whether a surface layer or buried layer in the pill.

A pill 106 produced at this stage of manufacturing is a useful commercial product to control nicotine cravings.

A means 108 is for disposing a compliance or persuading agent in the pill 106. Two kinds of compliance agents are preferred. One to make any usage tolerable, e.g., candy coating or flavors to mask the bitter taste of the nicotine compound. The other kind deters too much usage, e.g., abuse.

This second deterrent kind may depend on individual doses carrying small amounts of agent that accumulate to a threshold level when too many doses have been taken in a predetermined time. Another deterrent mechanism can depend on the parts "A" and "B" to produce a nasty part "C". ANTABUSE reacts this way with alcohol to make users violently ill. Many other component combinations like this exist in conventional commercial products.

Figure 2:
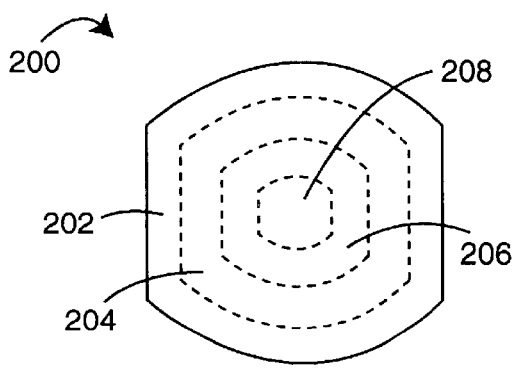
FIG. 2 is a cross sectional diagram of a pill embodiment of the present invention.

FIG. 2 illustrates a pill embodiment of the present invention, and is referred to by the general reference numeral 200. The pill 200 implements means 102 and 104 (FIG. 1), but does so twice. One inside the other. A coating 202 provides a compliance agent, but is otherwise inert. A bubble layer 204 comprises a compound of nicotine that is flash released in saliva when outer layer 202 is eroded. A more inner layer 206 provides a time delay to any flash release of a last nicotine payload 208. The time delay mimics that between puffs of a cigarette, or between whole cigarettes by a smoker. So the time delay can be a minute to ten minutes.

Figure 3:
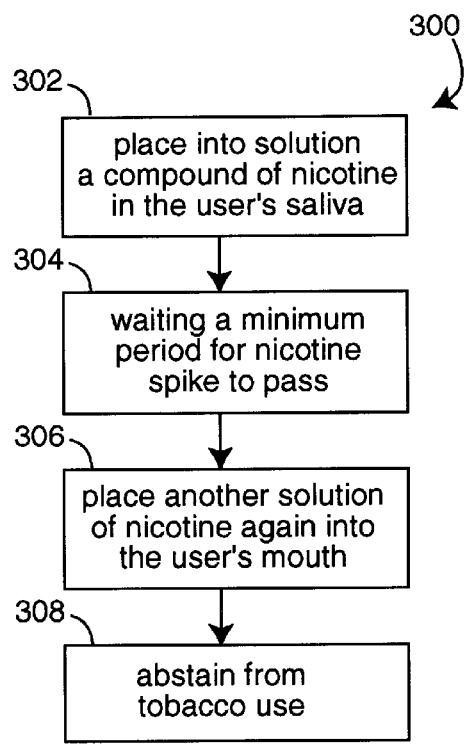
FIG. 3 is a flowchart of a quit-smoking embodiment of the present invention.

FIG. 3 represents a quit-smoking embodiment of the present invention, and is referred to by the general reference numeral 300. Such uses a means 302 to rapidly place nicotine into solution in the saliva of a user's mouth. A means 304 provides a mechanism for waiting between nicotine bursts. Such delay can be on the order of one to ten minutes. The mechanism can be as simple as burying layers inside layers, as in FIG. 2. Another mechanism includes taking separate pills at different times. A means 306 delivers a subsequent spike of nicotine through the mouth membranes of a user. A means 308 provides nicotine delivered in multiple bursts to the brain in the bloodflow of a user. The result is a smoker is relieved enough from addiction cravings to give up smoking, altogether or only temporarily.

Figure 4:
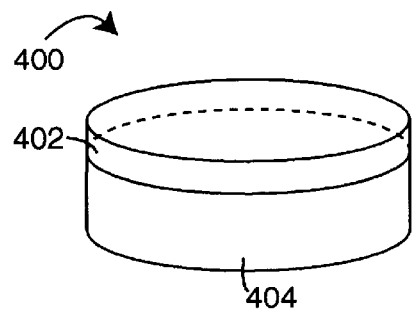
FIG. 4 is a perspective view of a layered oral tablet embodiment of the present invention.

FIG. 4 represents a transmucousal tablet embodiment of the present invention, and is referred to herein by the general reference numeral 400. The transmucousal tablet 400 provides a short pulse of nicotine into the bloodstream through the membranes of the mouth of a user. A thin nicotine layer 402 is disposed on a core 404, and is intended to flash dissolve in the mouth and be absorbed into the user's bloodflow to the brain via the heart and lungs. No nicotine is present in the core 404, it simply acts as a carrier of the nicotine. In other embodiments of the present invention, the core 404 further provides minerals, vitamins, good taste, and/or abuse-deterrents.

There are a number of method embodiments of the present invention for fabricating the thin nicotine layer 402 in the transmucousal tablet 400, and also FIGS. 1–3. For example, a syrup is prepared by mixing 0.2004 gram of sucrose, 0.2017 gram of nicotine, and 0.2034 gram of water. A thin layer of this syrup is spread with a paintbrush on top of a conventional antacid tablet, and allowed to dry. A wet layer typically preferably weighs 5.5 milligrams. In a test that was conducted, the tablet was 1.7 cm in diameter and 0.4 cm thick. The total weight of the tablet was 1.5767 grams. When such tablet is placed in the mouth, the nicotine layer dissolves and gives a short, intense pulse of about 1.8 milligrams of nicotine.

In a second method, a mixture is preferably made from 4.0289 grams of powdered calcium carbonate, 1.0683 grams of powdered magnesium hydroxide, 1.0856 grams of caffeine, and 40.4747 gram of powdered sucrose. One gram of the above mixture is placed in the cavity of a device used to prepare tablets. The material is compressed to form a compact tablet. A second mixture is preferably made of 0.6124 gram of nicotine tartrate and 8.0234 grams of sucrose. A conventional tablet-making device is opened, and 0.0823 gram of the second mixture is sprinkled on top of the previously manufactured tablet. The plunger of the conventional tablet-making device is reinserted and pressure applied to fuse the second mixture onto the previously manufactured tablet. The resulting compound tablet is removed. A nicotine layer is above and adherent to a non-nicotine layer. When this tablet is placed in the mouth, the nicotine layer dissolves to provide a short pulse of about one milligram of the nicotine base. The calcium carbonate and magnesium hydroxide have a basic reaction that promotes the absorption of the nicotine from nicotine tartrate. The addition of magnesium hydroxide to the calcium will reduce the tendency of the calcium to cause constipation.

A third method places one gram of the first mixture in the second method and places it in the cavity of a device for making tablets. The material is then compressed to a compact non-nicotine layer. The tablet-making device is opened, and 0.0631 gram of the second mixture of the second method is sprinkled on the top of the non-nicotine layer. The plunger is reinserted in the tablet-making device, and pressure is used to fuse the second mixture onto the non-nicotine layer thereby forming an overlying layer including nicotine.

The plunger is removed and 0.1256 gram of the first mixture from the second method is sprinkled on the top of the composite tablet. The plunger is reinserted into the cavity of the tablet-making device and pressure is used to fuse the new material on top of the tablet, thereby forming a overlying layer which does not include nicotine.

The plunger is removed and 0.0687 gram of the second mixture from the second method is sprinkled on top of the tablet. The plunger is again reinserted into the cavity of the tablet-making device and pressure is applied to form an overlying, nicotine layer and to fuse all of the layers together.

The resulting tablet thus has a first non-nicotine layer, a first nicotine layer, a second non-nicotine layer, and a second nicotine layer.

When placed in the mouth, the layers dissolves sequentially to provide two sharp pulses of nicotine separated by about one and a half minutes.

In a fourth method embodiment for making tablets, an exemplary syrup is prepared by mixing, e.g., 4.0412 grams of sucrose, 1.2018 grams of nicotine tartrate, and 10.6523 grams of water. An antacid tablet is dipped into the syrup and then allowed to dry. The original weight of the antacid tablet is 1.5465 grams. The tablet after dipping and drying preferably weighs 1.5678 grams. When this tablet is placed in the mouth, the layer including nicotine dissolves and gives a short, intense pulse of about 1.5 milligrams of nicotine.

A fifth method begins with a thick paste mixed, e.g., from 0.2134 gm of potato starch, 0.2246 gm of nicotine and 0.2107 gm of water. A brewer's yeast tablet is painted on one side with a confectioner's glaze, e.g., as marketed by Mantrose-Haeuser Company. Such glaze prevents nicotine paste from penetrating the brewer's yeast tablet. After the glaze has dried, the glazed brewer's yeast tablet preferably weighs 0.7478 gm. A thin layer of the aforementioned paste is painted on the glazed surface. The wet paste layer preferably weighs 5.2 milligrams, of which the nicotine is calculated to be 1.7 mg. The paste is allowed to dry. When this tablet is placed in the mouth, the layer including nicotine dissolves in a few seconds into the saliva of the mouth, and gives a short, intense nicotine pulse. Thereafter the brewer's yeast tablet along with the confectioner's glaze is swallowed.

In a sixth exemplary method embodiment of the present invention, a syrup is prepared by mixing 0.2104 gm of honey, 0.2137 gm nicotine and 0.2209 gm of water. Disks are punched from polyethylene sheeting. The disks are 12 mm in diameter and 0.67 mm in thickness. One of these disks preferably weighs 0.0736 gm. A thin layer of the aforementioned syrup is painted on top of the polyethylene disk. The wet layer preferably weighs 4.7 milligrams, of which 1.5 milligrams is nicotine. The syrup is allowed to dry. The resulting film is lightly dusted with amorphous colloidal silicon dioxide to reduce stickingness. When this tablet is placed in the mouth, the layer including nicotine dissolves in a few seconds and gives a short, intense nicotine pulse. Thereafter, the polyethylene disk is spat out.

In a seventh exemplary method embodiment of the present invention, a number of disks are punched from Whatman #1 qualitative filter paper. The disks are 12 mm in diameter and one of them typically preferably weighs 10.1 milligrams. A solution is preferably made by adding 0.2245 gm of nicotine to 0.5326 gm of water. A one-milliliter hypodermic syringe is partially filled with the nicotine solution. A small pendant drop, weighing 4.8 mg, is preferably made to appear on the tip of the hypodermic needle. Such small drop is then transferred to the filter disk. The nicotine solution is absorbed on the inert-to-nicotine cellulose fibers of the filter paper. The filter paper with its absorbed solution preferably weighs 14.9 milligrams, and is allowed to dry. The result is paper fibers coated with typically 1.4 mg of nicotine and empty space between the coated fibers. Such disk absorbs saliva when placed in the mouth. This dissolves the nicotine, and is absorbed by the tissues of the oral mucousal and/or the tongue. The result is a sharp, intense nicotine pulse. The small disk of filter paper may then be swallowed.

In an eighth exemplary method embodiment of the present invention, a number of disks are punched from DISOLVO, a trademarked water-soluble paper from D. Robbins & Company. The disks are 12 mm in diameter and 0.06 mm in thickness. One of these disks preferably weighs 7.2 milligrams. The disk is placed on a waterproof surface, e.g., a polypropylene specimen cup bottom. A solution is preferably made by adding 0.1552 gm of nicotine tartrate to 0.3259 gm of water. A hypodermic syringe is then used to place 14.1 milligrams of the nicotine tartrate solution on a DISOLVO disk. The somewhat swollen disk including the solution is allowed to dry on a waterproof surface. After drying, the paper regains its original appearance and is mechanically self-supporting. Such paper disk rapidly disintegrates in the saliva of the mouth and gives a nicotine pulse.

In a ninth exemplary method embodiment of the present invention, disks are punched from sheets of DISOLVO. The disks are 12 mm in diameter and 0.06 mm in thickness. One of these disks preferably weighs 7.2 milligrams. The disk is placed on a waterproof surface like in the eighth method. A small amount of nicotine base is drawn into a one-milliliter hypodermic syringe. A small pendant drop is preferably made to appear on the tip of the hypodermic syringe needle. Small drops such as these, were experimentally found to include a calculated 1.2 milligrams of nicotine base. This is then transferred to the disk, which absorbed it. The disk with the added nicotine preferably weighs 8.4 milligrams. Such paper disk, when placed in the mouth, rapidly disintegrates in the saliva of the mouth and gives a sharp, intense nicotine burst.

In a tenth exemplary method embodiment of the present invention, a solution of nicotine citrate is preferably made by adding 0.1847 gm of nicotine base, 0.2047 gm of citric acid and 0.5267 gm of water. A hypodermic syringe is then used to place 9.5 milligrams of this solution, of which 1.8 mg is nicotine base, on a DISOLVO disk. The disk with the nicotine citrate is allowed to dry on the waterproof surface. Such disk when placed in the mouth, rapidly disintegrates in the saliva and gives a nicotine pulse, less sharp and intense than the base.

In an eleventh exemplary method embodiment of the present invention, an ALTOID cinnamon flavored mint is painted on one side with a confectioner's glaze made by Mantrose-Haeuser Company. The glaze prevents the nicotine from penetrating the confection. The glaze is allowed to dry and the mint with the dried glaze preferably weighs 0.6977 gm. A solution is preferably made by mixing and heating 0.2678 gm of KNOX unflavored gelatin and 0.5893 gm of water. The gelatin solution is allowed to cool and 0.2145 gm of nicotine base is added and dispersed uniformly throughout the gelatin solution. A thin layer of the nicotine-gelatin solution is spread on the dried glaze. The coated tablet preferably weighs 0.7065 gm. From the difference in tablet weights and the nicotine concentration in the coating the nicotine content is calculated to be about 1.7 mg. The gelatin layer gels in a few minutes. When this tablet is placed in the mouth, the layer including nicotine dissolves in the saliva in a few seconds, and gives a sharp intense nicotine pulse. Thereafter the mint is allowed to dissolve in the mouth and is swallowed.

In a twelfth exemplary method embodiment of the present invention, a solution of citric acid is prepared by dissolving 0.1687 gm of citric acid in 0.3323 gm of water. Then 0.0121 gm of nicotine citrate, of nineteen percent nicotine base, is applied to a DISOLVO disk on a waterproof surface. The disk with the nicotine citrate solution of 2.3 mg nicotine is allowed to dry. Then, 0.0317 gm of citric acid solution, 0.01 g citric acid, is added and allowed to dry. Such disk when placed in the mouth rapidly disintegrates and gives a more moderate pulse of nicotine.

In a thirteenth exemplary method embodiment of the present invention, a solution is preferably made by adding 0.1728 gm of water to 0.2305 gm of a nicotine sulfate solution which includes forty percent nicotine base. The resulting solution includes 22.9 percent nicotine base. About 7.4 mg of this solution, 1.6 mg nicotine, is absorbed in a 12 mm disk of Watman #1 filter paper. The disk is then dried. A few milligrams of sodium bicarbonate is sprinkled on the nicotine including disk. The sodium bicarbonate is pressed into the pores of the filter paper by placing it between two sheets of 4 mil polyethylene and pressing it with a small spatula. About 3.6 milligrams of sodium bicarbonate will be imbedded in the filter paper. The resulting disk when placed in the mouth gives a very rapid nicotine pulse, comparable to nicotine base administrations. In another variation of this example, the paper surface is roughened by lightly abrading it with needle-point tweezers. A quantity of sodium bicarbonate is placed on the surface. When smoothed out with a spatula, the fibers bind the bicarbonate powder, giving a paper surface less prone to shed bicarbonate particles. Such provides an intimate mechanical composite of nicotine-salt-impregnated or coated paper fibers surrounding powdered sodium bicarbonate.

In a fourteenth exemplary method embodiment of the present invention, an irregularly-shaped piece of Watman #1 paper weighing 11.9 mg is fabricated. About 14.3 mg of a nicotine tartrate solution including 11.5 percent nicotine is injected into the paper, and allowed to dry. The performance of this paper when placed in the mouth is indistinguishable from similar ones on circular disks.

In a fifteenth exemplary method embodiment of the present invention, disks of nicotine including DISOLVO paper are made, each layer including 0.5 to 5 milligrams of nicotine. Bicarbonate may be added to amplify the effective nicotine pulse. Dissolution of the nicotine layer is less than one minute, preferably less than thirty seconds. The preferred layer is a coating which does not immediately dissolve, e.g., confectioner's glaze. The dissolution time of the nicotine-including layer is at least as long as the dissolution time of other layer. Layer is a slow-dissolving non-toxic layer of material. A cast sugar film such as LIFE-SAVERS™, the popular candy, is appropriate, as would a gelatin film. Dissolution in saliva in the mouth is extended to more than the nicotine including layers, e.g., in the range of one to twenty minutes. Recognizable separate pulses of nicotine are released to the user. The spacing between nicotine bursts is a function of the desired effect on the senses of the user. Since a single nicotine pulse has an onset time of about thirty seconds, this sets the minimum spacing between pulses.

In an alternative multi-layered embodiment, one layer is a slow-dissolving layer, such as a cast sugar film. It dissolves in one to twenty minutes, more preferably one to five minutes, and a sharp pulse of nicotine is experienced. A second layer then dissolves in one to five minutes to expose another nicotine layer. Such delivers a second sharp nicotine pulse in less than one minute.

A nicotine-including layer may be disposed separately on both sides of a flat, slow-dissolving layer. Alternatively, such may completely surround the layer. The slow-dissolving layer preferably completely surrounds nicotine layer to ensure a time delay between the nicotine pulses experienced by the user.

Embodiments of the present invention can be made with graduated concentrations of nicotine. Smokers take decreasing doses over days or weeks to break free of their addiction to nicotine and smoking. Such can supply the usual dose of nicotine normally obtained from smoking, while avoiding exposure to the toxic and carcinogenic combustion products.

Many alternative ways are available to engineer rapidly dissolving nicotine layers, e.g., the geometry of the tablet, the thickness of the layers, and the materials employed. In a preferred embodiment of this invention, the layer that includes nicotine or nicotine-including compounds will dissolve in less than two minutes. The materials other than nicotine or nicotine including compounds can include sugars, non-nutritive sweeteners, coloring agents, flavoring agents, effervescent agents, binders, and other compatible materials.

It is therefore an object of the instant invention to provide an aversive experience when too many tablets are taken in too short a time. A multiplicity of aversive sensations is preferable, wherein each aversive sensation by itself is tolerable.

The combination of sensations aversive at a sufficient level or in sufficient combination, may be incorporated within a single tablet. One may also incorporate different embodiments of the instant invention, such that there is a high probability that the use of a multiplicity of the instant tablet will result in an even more aversive sensation experience due to the more aversive combination of aversive sensations, whether taste or other sensations.

Many chemicals induce sensations which may not be one of the five recognized taste sensations and yet may be a sensation received by the tongue, skin or mucous membranes.

The part of the tablet not including nicotine can be anything that is acceptable to take by mouth. It can be inert as, for example, filter paper or plastic. It can be in any shape in any size, of any dimension or dimensionality, subject only to being able to be taken orally. It can include caffeine, vitamins, flavoring materials, buffering agents, sugars, non-nutritive sweeteners, materials giving bitter, hot, painful or other tastes or sensations tolerable at some level but intolerable at a higher level, and other compatible materials.

An oral tablet embodiment of the present invention comprises a payload for fixing a compound of nicotine, a carrier for delivering the payload to the mouth of a tobacco-addicted user, a release mechanism for dispersing the compound of nicotine when immersed in saliva, and a pulse mechanism for a sudden release of the compound of nicotine. This provides a burst of nicotine for absorption into the bloodstream of a user to circulate to the brain before passing through the liver. Such embodiments can be extended by adding a repeating-pulse mechanism for providing more than one sudden release of the compound of nicotine, and a quiescent mechanism for separating each sudden release from the next. In still further embodiments of the present invention, there is added a disintegrating mechanism for eroding the carrier to expose the payload.

Although particular embodiments of the present invention have been described and illustrated, such is not intended to limit the invention. Modifications and changes will no doubt become apparent to those skilled in the art, and it is intended that the invention only be limited by the scope of the appended claims.

What is claimed is:

1. An oral tablet, comprising:
 a paper disk of absorbent and saliva-dissolvable material; and
 a nicotine base in liquid form deposited on and absorbed by the paper disk;
 wherein, the nicotine base further includes citric acid and water, and the combined mixture weighs about 9.5 milligrams before being allowed to dry on the paper disk, wherein about 1.8 milligrams is nicotine available for absorption in said mouth of a user;

wherein, such combination provides for the delivery of a sharp, intense burst of the nicotine base when exposed to saliva in a mouth of said user.

2. An oral tablet, comprising:

a paper disk of absorbent and saliva-dissolvable material; and a nicotine base in liquid form deposited on and absorbed by the paper disk;

wherein such combination provides for the delivery of a sharp, intense burst of the nicotine base when exposed to saliva in a mouth of a user;

wherein, the nicotine base includes nicotine citrate, of which about nineteen percent is nicotine, wherein the nicotine citrate weighs about 2.3 milligrams before being allowed to dry on the paper disk, and further includes another application of citric acid solution to moderate said burst of nicotine.

3. An oral tablet, comprising:

a disk of polyethylene that is eventually spat out by a user; and a syrup base in liquid form deposited on and absorbed by the disk of polyethylene, and comprising a mixture of honey, nicotine, and water in approximately equal proportions;

wherein, such combination provides for the delivery of a sharp, intense burst of the nicotine base when exposed to saliva in a mouth of a user before being spat out.

4. The oral tablet of claim 3, wherein:

the disk of polyethylene is about twelve millimeters in diameter, is about 0.67 millimeters thick, and weighs about 73.6 milligrams; and the syrup base weighs about 4.7 milligrams total, with about 1.7 milligrams of that being nicotine, before said is deposited and allowed to dry.

* * * * *